(12) United States Patent
Anderson et al.

(10) Patent No.: US 7,848,824 B2
(45) Date of Patent: Dec. 7, 2010

(54) SEALED MEDICAL ELECTRODE PACKAGE

(75) Inventors: John McCune Anderson, Hollywood (GB); Johnny Houston Anderson, Hollywood (GB); James Allen, Ballyclare (GB)

(73) Assignee: Heartsine Technologies Limited, Belfast (GB)

( * ) Notice: Subject to any disclaimer, the term of this patent is extended or adjusted under 35 U.S.C. 154(b) by 424 days.

(21) Appl. No.: 11/575,087

(22) PCT Filed: Sep. 21, 2005

(86) PCT No.: PCT/IB2005/003692

§ 371 (c)(1),
(2), (4) Date: Dec. 18, 2007

(87) PCT Pub. No.: WO2006/033021

PCT Pub. Date: Mar. 30, 2006

(65) Prior Publication Data

US 2008/0210592 A1      Sep. 4, 2008

(30) Foreign Application Priority Data

Sep. 22, 2004 (IE) .............................. S2004/0642
Apr. 21, 2005 (IE) .............................. S2005/0242

(51) Int. Cl.
*A61N 1/00* (2006.01)
(52) U.S. Cl. ...................................................... 607/142
(58) Field of Classification Search ................ 600/392, 600/386; 607/142, 122; 206/210, 701, 370
See application file for complete search history.

(56) References Cited

U.S. PATENT DOCUMENTS

| 4,034,854 | A  | * | 7/1977  | Bevilacqua ............... 206/370 |
| 4,777,954 | A  | * | 10/1988 | Keusch et al. ............ 600/392 |
| 4,827,939 | A  | * | 5/1989  | Cartmell et al. ........... 600/392 |
| 5,402,884 | A  | * | 4/1995  | Gilman et al. ............. 206/701 |
| 6,694,193 | B2 | * | 2/2004  | Lyster et al. .............. 607/142 |
| 7,668,604 | B2 | * | 2/2010  | O'Connor et al. ......... 607/152 |
| 2002/0117408 | A1 | * | 8/2002 | Solosko et al. ........... 206/210 |
| 2003/0055478 | A1 | * | 3/2003 | Lyster et al. ............. 607/142 |

* cited by examiner

*Primary Examiner*—George Manuel
*Assistant Examiner*—Robert N Wieland
(74) *Attorney, Agent, or Firm*—Porter Wright Morris & Arthur LLP

(57) ABSTRACT

A sealed medical electrode package comprises first and second electrodes each comprising a conductive layer (14) disposed on one major surface of a flexible nonconductive backing sheet (10). The electrodes are disposed with their conductive layers (14) face-to-face and their backing sheets separably sealed together around their peripheral edges so that the backing sheets form a substantially gas-impermeable enclosure containing the conductive layers. In an alternative embodiment (FIG. 6) a respective electrical contact extends through each backing sheet into electrical contact with the respective conductive layer, and a substantially gas-impermeable packaging material encloses the electrodes. The packaging material has a respective aperture exposing each electrical contact, the periphery of each aperture being sealed to the backing sheet around the respective contact.

15 Claims, 4 Drawing Sheets

SEALED MEDICAL ELECTRODE PACKAGE

This invention relates to a sealed medical electrode package.

Medical electrodes used, for example, in external cardiac defibrillators typically have a flexible non-conductive backing sheet bearing a conductive gel layer. Since the gel layer rapidly deteriorates if left open to the atmosphere, such electrodes are normally sealed, usually in pairs, in a gas-impermeable package which is opened just before the electrodes are deployed for use. There are several known techniques for packaging such electrodes, but all require some form of outer protective packaging which needs to be removed before the electrodes themselves are handled by the operator.

It is an object of the invention to provide an improved sealed medical electrode package which can be manufactured more cheaply and simply than existing packages while still protecting the conductive layers against the external environment.

Accordingly, a first aspect of the invention provides a sealed medical electrode package comprising first and second electrodes each comprising a conductive layer disposed on one major surface of a flexible non-conductive backing sheet, the electrodes being disposed with their conductive layers face-to-face and their backing sheets separably sealed together around their peripheral edges so that the backing sheets form a substantially gas-impermeable enclosure containing the conductive layers, each conductive layer having a respective electrical connector.

The first aspect of the invention provides a technique whereby there is no extra external outer packaging needed to protect the environmentally sensitive elements of the electrodes, thereby retaining shelf life, using a method which also allows easy rapid deployment while significantly reducing production cost.

According to a second, independent aspect of the invention there is provided a sealed medical electrode package comprising first and second electrodes each comprising a conductive layer disposed on one major surface of a flexible non-conductive backing sheet, the electrodes being disposed with their conductive layers face-to-face, a respective electrical contact extending through each backing sheet into electrical contact with the respective conductive layer, and a substantially gas-impermeable packaging material enclosing the electrodes, the packaging material having a respective aperture exposing each electrical contact, the periphery of each aperture being sealed to the backing sheet around the respective contact.

Embodiments of the invention will now be described, by way of example, with reference to the accompanying drawings, in which.

It will be understood that the drawings are not to scale and that, in particular, the thicknesses of the various layers shown in FIGS. 1 to 4 and 6 has been greatly exaggerated.

Figure 1:
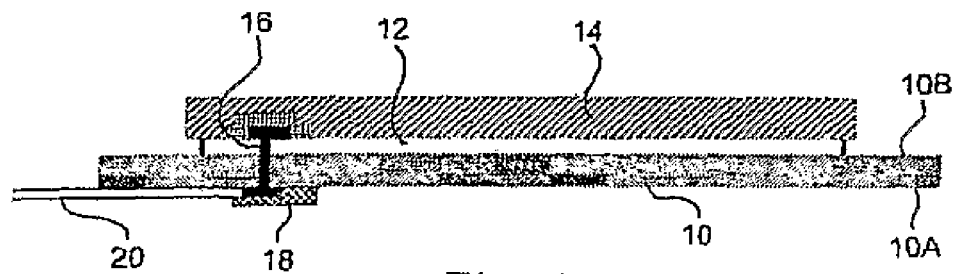
FIG. 1 is a schematic cross section through a typical medical electrode according to the prior art.

FIG. 1 is a cross section through a conventional hydrogel electrode used, for example, for external cardiac defibrillation or medical monitoring. It comprises a flexible non-conductive backing sheet 10 made, for example, of a thin flexible polymer, and having opposite major surfaces 10A and 10B. A conductive layer 12 is deposited on the surface 10B and a final conductive gel layer 14 is deposited on the layer 12, the gel layer 14 being designed for interface with a patient's skin. The conductive layer 12 is preferably a homogeneous, solid, thinly deposited metal layer or a conductive ink. The gel layer 14 is preferably a hydrogel layer. Suitable materials for the layers 12 and 14 are well known in the art. A conductive stud 16 extends through the backing sheet 10 to the interface between the layers 12 and 14. The stud 16 is designed to accept a snap-on connector 18 at one end of a lead wire 20. Alternatively, the lead wire 20 could be fixed to the stud 16. These arrangements allow electrical connection to the gel layer 14 while the electrode is in position and deployed on a patient. The construction of this type of stud connection is well know to those skilled in the art.

As mentioned, electrodes of the type shown in FIG. 1 are usually packaged in pairs in a separate outer package. The embodiment of the first aspect of the invention, FIGS. 2 to 5, avoids the need for a separate outer package. In FIGS. 2 to 5 the same reference numerals have been used for the same or equivalent components of FIG. 1.

Figure 2:
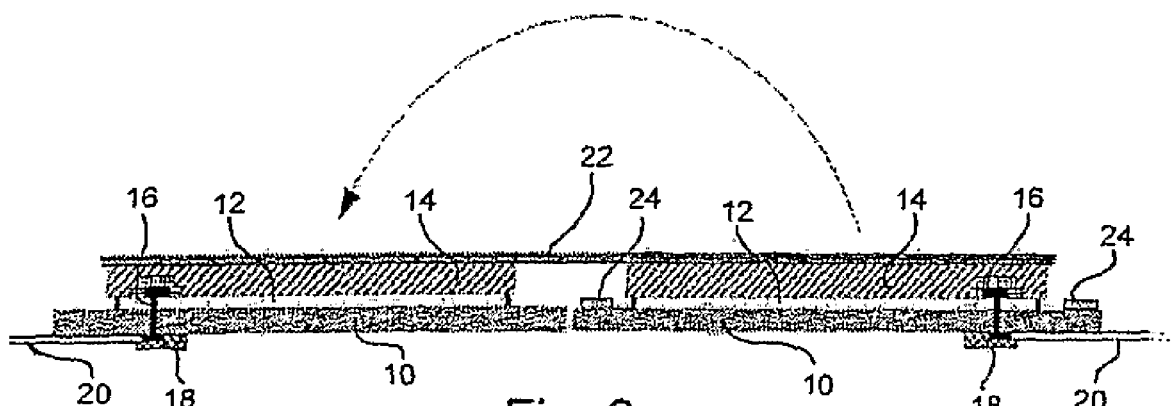
FIGS. 2 to 4 are schematic cross-sections showing successive stages in the manufacture of an electrode package according to an embodiment of the first aspect of the invention.

FIG. 2 shows two electrodes of the type described with reference to FIG. 1 laid end-to-end with a common release liner 22 applied to the exposed surfaces of the gel layers 14. The release liner 22 protects the adhesive nature of the gel layers and typically comprises a silicon-coated paper base.

Figure 3:
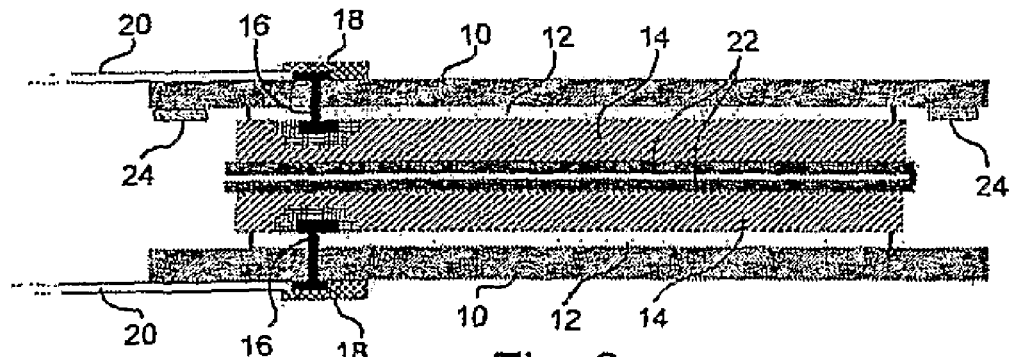

Now, as indicated by the arrow in FIG. 2, the two electrodes are folded over one upon and in register with the other so that their respective conductive gel layers 14 are disposed face-to-face, FIG. 3, with the release liner 22 intervening between the two facing surfaces of gel layers. As seen in FIG. 2, a continuous line of adhesive 24 extends around the peripheral edge of the backing sheet 10 of the right hand electrode (as seen in FIG. 2). After the electrodes have been folded over as seen in FIG. 3 the peripheral edges of the two backing sheets are pressed together to hermetically seal the edges, FIGS. 4 and 5. This forms a gas-impermeable pocket containing the gel electrodes 14.

A pair of tabs 26 are provided, each attached to, or integral with, a respective backing sheet 10. These tabs allow the two electrode backing sheets be peeled apart along the line of adhesive, thereby separating the electrodes for deployment and use. Once opened, the release liner 22 can be peeled away and the electrodes placed upon the patient. In the preferred embodiment the adhesive is a biocompatible heat sensitive glue (i.e. liquid when heated) which retains the backing sheets 10 hermetically sealed under normal handling yet allows them to be peeled apart without damage to either. Glue with these characteristics is well known to those skilled in the art. If desired the tabs 26 may be integral extensions of the backing sheets 10, rather than separately attached. In such case, the adhesive would not extend on to the tabs.

The foregoing has assumed that the backing sheets 10 are separable along the line of the adhesive 24. However, if a permanent adhesive is used the backing sheets 10 can be separated by providing a line of weakening 28, FIG. 5, along the inside of the adhesive, so that the sheets 10 tear along this line as they are separated. Of course, any such line of weakening must not significantly allow the ambient atmosphere to enter the interior of the package before the package is opened.

In an alternative embodiment the peripheral edges of the two backing sheets 10 are sealed by a clamping ring. The ring is in two circumferential halves that snap together to form a single ring running around and sealing the peripheral edges of the backing sheets 10. This ring gives the electrodes a general rigidity. In this case the backing layers 10 have a line of weakening 28 on the inside of the clamping ring. The electrodes can then be readily torn out of the ring to separate them and open the protective pocket.

Figure 6:
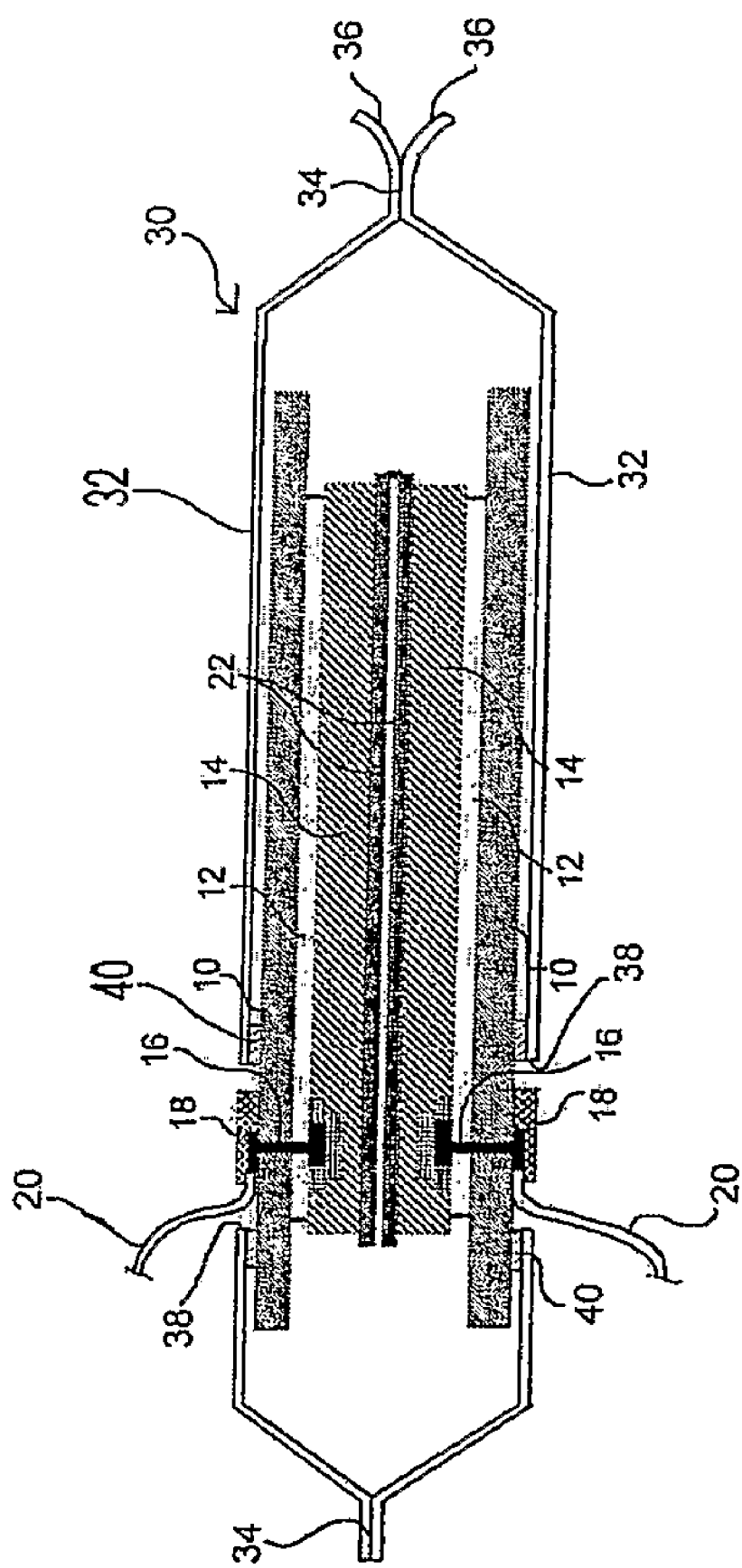
FIG. 6 is a schematic cross-section through an electrode package according to an embodiment of the second aspect of the invention.
Figure 7:
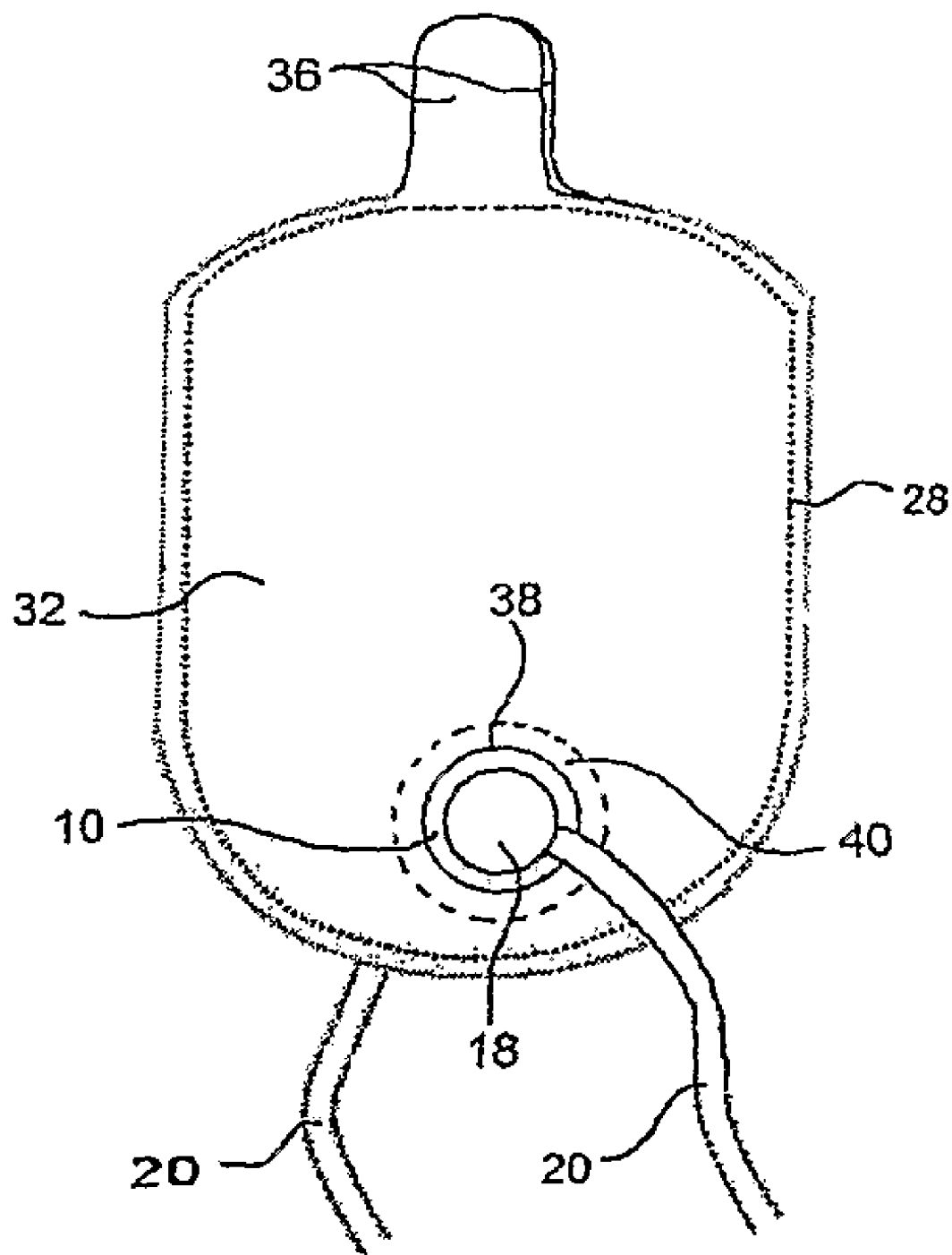
FIG. 7 is a plan view of the final electrode package of FIG. 6.

FIGS. 6 and 7 show an electrode package according to an embodiment of the second aspect of the invention. In FIGS. 6 and 7 components the same as or equivalent to those of FIGS. 1 to 5 and have been given the same reference numerals. To avoid unnecessary repetition, only the differences from the embodiment of FIGS. 1 to 5 will be described.

Figure 4:
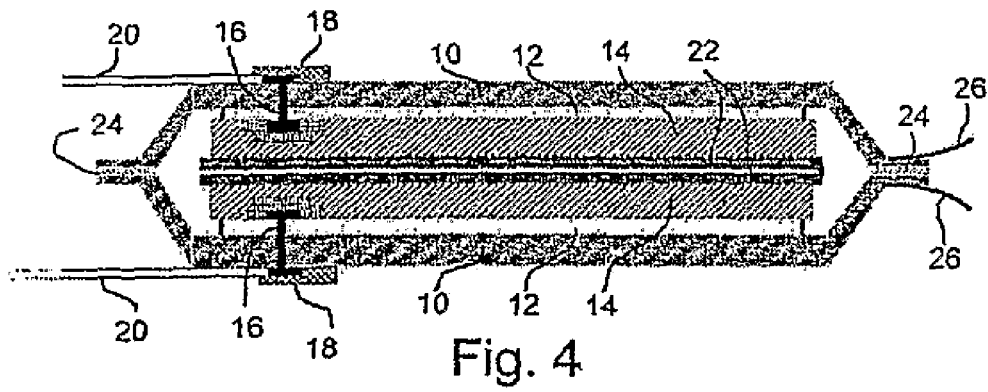
Figure 5:
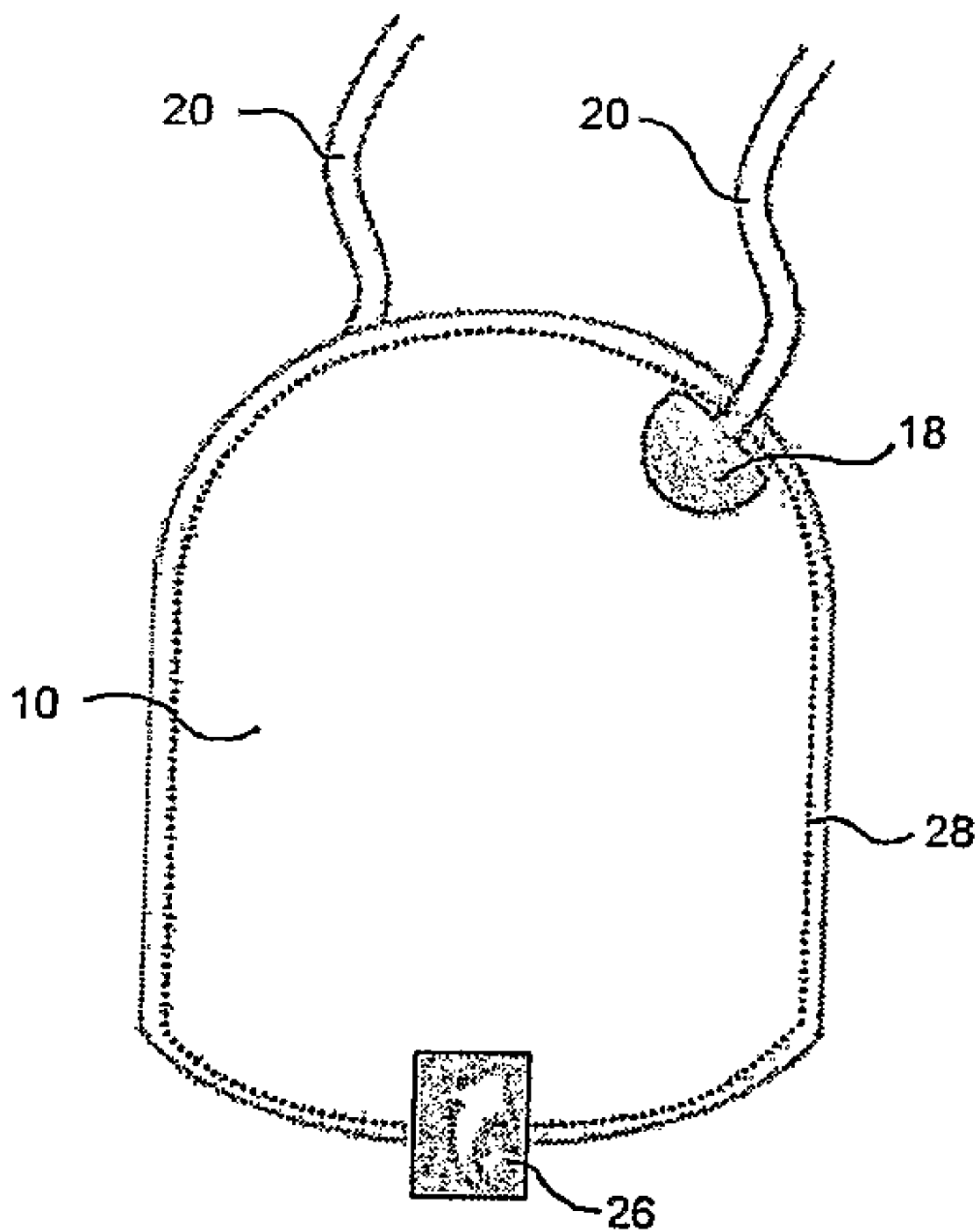
FIG. 5 is a plan view of the final electrode package of FIG. 4.

In the package of FIGS. 6 and 7 the peripheral edges of the backing sheets 10 are not sealed together as shown in FIG. 4 of the previous structure. Instead, the two electrodes, each comprising the layers 10, 12 and 14, are enclosed in an envelope or pocket 30 comprising two flexible sheets 32 of gas-impermeable material of a kind well-known in the art. The sheets 32 are heat-sealed at their periphery 34 and a pair of tabs 36 are each integral with, or fixed to, a respective sheet 32 to allow them to be peeled apart.

To allow the conductive studs 16 and associated lead wires 20 to be accessible without opening the package, each sheet 32 has a respective aperture 38 surrounding each stud 16 at a distance and exposing each stud 16 for connection to the lead 20. To maintain the gas-tight integrity of the package, the periphery of each aperture 38 is sealed, e.g. by a peel-to-release adhesive 40, to the respective backing sheet 10.

The invention is not limited to the embodiments described herein which may be modified or varied without departing from the scope of the invention.

The invention claimed is:

1. A sealed medical package comprising first and second electrodes each comprising a conductive layer disposed on one major surface of a flexible non-conductive backing sheet, the electrodes being disposed with their conductive layers face-to-face and their backing sheets separately sealed together around their peripheral edges so that the backing sheets form a substantially gas-impermeable enclosure containing the conductive layers, each conductive layer having a respective electrical connector.

2. A package as claimed in claim 1, wherein each electrical connector comprises an electrical contact extending through a respective backing sheet into electrical contact with the respective conductive layer.

3. A package as claimed in claim 2, wherein each conductive layer comprises a conductive gel and a release liner is disposed between the facing surfaces of the conductive layers.

4. A package as claimed in claim 3, wherein the peripheral edges are sealed together by adhesive.

5. A package as claimed in claim 2, wherein the peripheral edges are sealed together by adhesive.

6. A package as claimed in claim 1, wherein each conductive layer comprises a conductive gel and a release liner is disposed between the facing surfaces of the conductive layers.

7. A package as claimed in claim 6, wherein the peripheral edges are sealed together by adhesive.

8. A package as claimed in claim 1, wherein the peripheral edges are sealed together by adhesive.

9. A package as claimed in claimed in any one of claims 1-8, further including a pair of tabs each fixed to or integral with a respective backing sheet to allow the electrodes to be pealed apart.

10. A sealed medical electrode package comprising first and second electrodes each comprising a conductive layer disposed on one major surface of a flexible non-conductive backing sheet, the electrodes being disposed with their conductive layers face-to-face, a respective electrical contact extending through each backing plate sheet into electrical contact with the respective conductive layer, and a substantially gas-impermeable packaging material enclosing the electrodes, the packaging material having a respective aperture exposing each electrical contact, the periphery of each aperture being sealed to the backing sheet around the respective contact.

11. A package as claimed in claim 10, wherein the packaging material comprises two packaging sheets enclosing the electrodes between them and releasably sealed together around their peripheral edges.

12. A package as claimed in claim 11, further including a pair of tabs each fixed to or integral with a respective packaging sheet to allow the packaging sheets to be peeled apart.

13. A package as claimed in claim 11, wherein the peripheral edges of the packaging sheets are heat-sealed together.

14. A package as claimed in claim 12, wherein the peripheral edges of the packaging sheets are heat-sealed together.

15. A package as claimed in any one of claims 10 to 13 and 14, wherein each conductive layer comprises a conductive gel and a release liner is disposed between the facing surfaces of the conductive layers.

\* \* \* \* \*